United States Patent
Konishi

(10) Patent No.: US 8,986,288 B2
(45) Date of Patent: Mar. 24, 2015

(54) MEDICAL SYSTEM

(71) Applicant: Olympus Medical Systems Corp., Tokyo (JP)

(72) Inventor: Sumihito Konishi, Akishima (JP)

(73) Assignee: Olympus Medical Systems Corp., Tokyo (JP)

( * ) Notice: Subject to any disclaimer, the term of this patent is extended or adjusted under 35 U.S.C. 154(b) by 46 days.

(21) Appl. No.: 13/938,737

(22) Filed: Jul. 10, 2013

(65) Prior Publication Data

US 2014/0031706 A1    Jan. 30, 2014

Related U.S. Application Data

(63) Continuation of application No. PCT/JP2012/077842, filed on Oct. 29, 2012.

(60) Provisional application No. 61/588,353, filed on Jan. 19, 2012.

(51) Int. Cl.
*H03G 3/20* (2006.01)
*A61B 18/00* (2006.01)
*A61B 5/0402* (2006.01)
*A61B 5/04* (2006.01)

(52) U.S. Cl.
CPC *H03G 3/20* (2013.01); *A61B 18/00* (2013.01); *A61B 5/04* (2013.01)
USPC .................................................. 606/1; 606/34

(58) Field of Classification Search
CPC ...... A61B 5/7415; A61B 5/746; A61B 18/00; A61B 5/7405
USPC ........................................................... 606/38
See application file for complete search history.

(56) References Cited

U.S. PATENT DOCUMENTS

| 5,318,563 | A | 6/1994 | Malis et al. |
| 6,402,741 | B1 | 6/2002 | Keppel et al. |
| 2008/0015473 | A1 | 1/2008 | Shimizu |

(Continued)

FOREIGN PATENT DOCUMENTS

| EP | 1 806 108 A1 | 7/2007 |
| EP | 2 468 203 A1 | 6/2012 |

(Continued)

OTHER PUBLICATIONS

Jan. 15, 2013 International Search Report issued in International Application No. PCT/JP2012/077842 (with translation).

(Continued)

*Primary Examiner* — Michael Peffley
*Assistant Examiner* — Bo Ouyang
(74) *Attorney, Agent, or Firm* — Oliff PLC

(57) ABSTRACT

A high-frequency output apparatus and an ultrasound output apparatus, which are medical apparatuses, each has a CPU, a communication circuit and a speaker. Each CPU transmits, when an output volume level of a sound outputted from its own speaker is changed, information about the changed output volume level to the other medical apparatus from the communication circuit, and controls output volume of the sound outputted from its own speaker on the basis of output volume information about a sound outputted of the speaker of the other apparatus, which has been received in the communication circuit.

12 Claims, 10 Drawing Sheets

(56) References Cited

U.S. PATENT DOCUMENTS

2009/0131929 A1* 5/2009 Shimizu .......................... 606/34
2011/0273465 A1* 11/2011 Konishi et al. ................ 345/589

FOREIGN PATENT DOCUMENTS

| JP | A-2003-199768 | 7/2003 |
| JP | U-3111214 | 7/2005 |
| JP | B2-4755106 | 8/2011 |
| JP | B2-4997344 | 8/2012 |
| WO | WO 2006/035659 A1 | 4/2006 |
| WO | WO 2011/052390 A1 | 5/2011 |

OTHER PUBLICATIONS

Aug. 27, 2013 Office Action issued in Japanese Patent Application No. 2013-530442 (with translation).

* cited by examiner

US 8,986,288 B2

MEDICAL SYSTEM

CROSS REFERENCE TO RELATED APPLICATION

This application is a continuation application of PCT/JP2012/077842 filed on Oct. 29, 2012 and claims benefit of U.S. Provisional Patent Application No. 61/588,353 filed in the U.S.A. on Jan. 19, 2012, the entire contents of which are incorporated herein by this reference.

BACKGROUND OF THE INVENTION

1. Field of the Invention

The present invention relates to a medical system, and in particular to a medical system including multiple medical apparatuses each of which is provided with a sound output function.

2. Description of the Related Art

Conventionally, there may be a case where multiple medical apparatuses are used in an operation. For example, there may be a case where an ultrasound output apparatus and a high-frequency output apparatus, which are apparatuses for performing dissection and coagulation of living tissue, are used together.

The ultrasound output apparatus is an apparatus for performing treatment for treatment-target living tissue by ultrasound vibration, and the high-frequency output apparatus is an apparatus for performing the treatment by a high-frequency current. These medical apparatuses are placed in an operating room and used according to a treatment-target site, a treatment purpose and the like.

Some medical apparatuses have a function of outputting a sound. For example, when a surgeon presses down a switch for specifying energy output for treatment to perform energy output, the medical apparatus outputs a predetermined sound at predetermined volume in order to notify the surgeon or cause the surgeon to recognize that energy for the treatment is being outputted. Such a sound output function is provided for each apparatus, and volume is set for each apparatus.

In some conventional medical systems, two medical apparatuses communicate with each other when the two medical apparatuses are used together, for example, as proposed in the specification of U.S. Patent Application Publication No. 2008/0015473.

Some pieces of medical equipment have a speaker and output an instruction by a sound or a voice message as proposed in the specification of U.S. Pat. No. 6,402,741 or the specification of U.S. Pat. No. 5,318,563.

SUMMARY OF THE INVENTION

A medical system of an aspect of the present invention is a medical system including a first medical apparatus and a second medical apparatus, the medical system including: a first output state detecting section provided for the first medical apparatus, the first output state detecting section detecting a first output state about a first output; a second output state detecting section provided for the second medical apparatus, the second output state detecting section detecting a second output state about a second output; a first sound outputting section provided for the first medical apparatus, the first sound outputting section outputting a first sound corresponding to the first output state detected by the first output state detecting section; a second sound outputting section provided for the second medical apparatus, the second sound outputting section outputting a second sound corresponding to the second output state detected by the second output state detecting section; a second sound output controlling section controlling output of the second sound outputted from the second sound outputting section according to the second output state detected by the second output state detecting section; a first output volume information transmitting section provided for the first medical apparatus, the first output volume information transmitting section transmitting output volume information about the first sound to the second medical apparatus; a second output volume information receiving section provided for the second medical apparatus, the second output volume information receiving section receiving the output volume information transmitted from the first output volume information transmitting section; and a second output volume adjusting section provided for the second sound output controlling section, the second output volume adjusting section setting reference volume of the second sound outputted by the second sound output on the basis of the output volume information, making a setting for lowering the reference volume of the second sound when a sound indicating error occurrence in the apparatus is outputted from the first sound outputting section, and returning the second sound to the reference volume when the error occurrence stops in the first sound outputting section.

DETAILED DESCRIPTION OF THE PREFERRED EMBODIMENT

The present invention will be described below by an embodiment.
(System Configuration)

Figure 1:
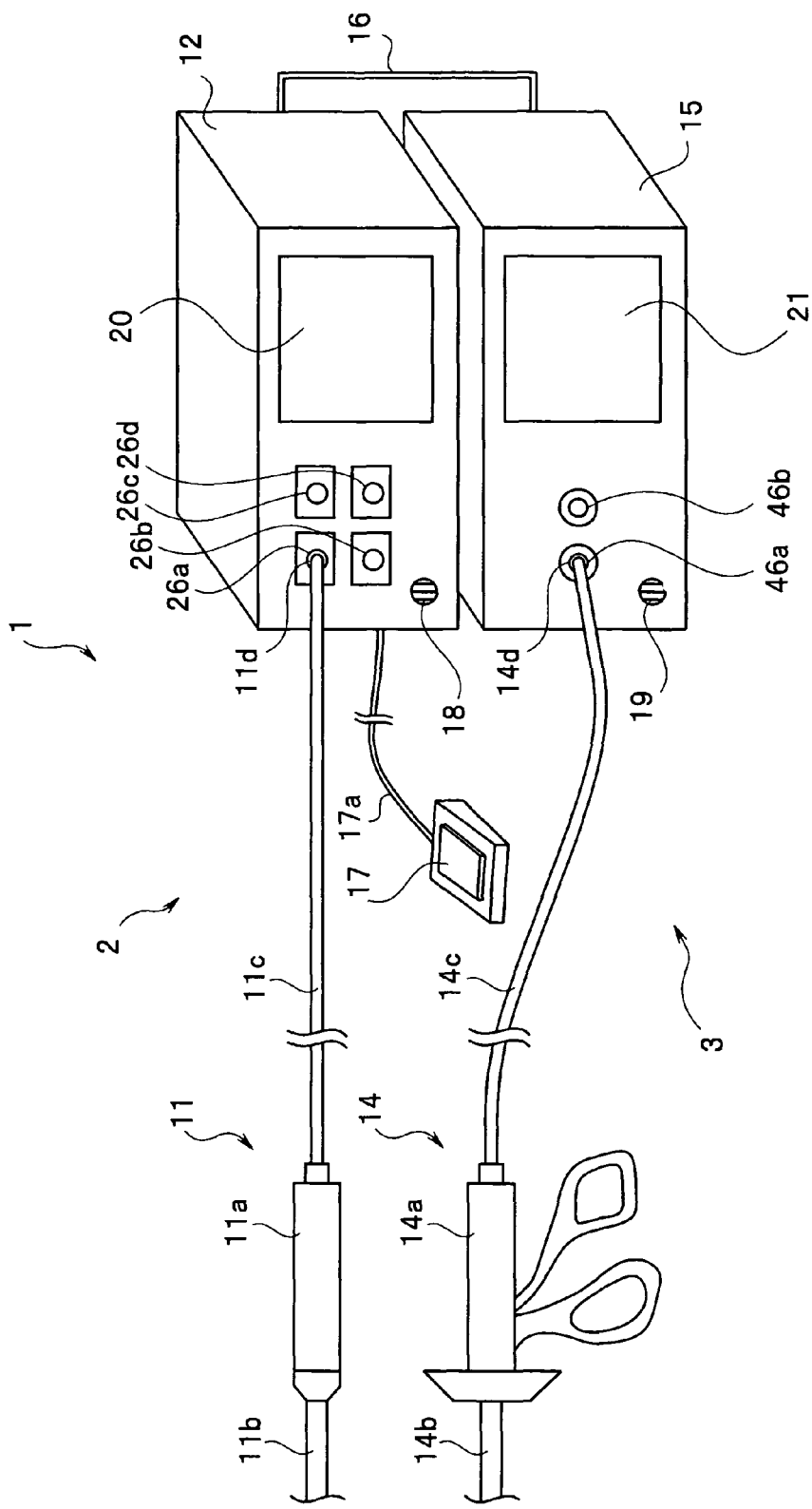
FIG. 1 is a configuration diagram showing a configuration of an operation system 1 according to an embodiment of the present invention.

FIG. 1 is a configuration diagram showing a configuration of an operation system according to an embodiment of the present invention. An operation system 1 is a medical system configured including a high-frequency treatment apparatus 2 and an ultrasound treatment apparatus 3.

The high-frequency treatment apparatus 2 is a medical apparatus having a handpiece 11 as a treatment instrument which performs treatment for treatment-target living tissue by a high-frequency current and a high-frequency output apparatus 12 which outputs a high-frequency current to the handpiece 11. The ultrasound treatment apparatus 3 is a medical apparatus having a handpiece 14 as a treatment instrument which performs treatment for treatment-target living tissue by ultrasound vibration and an ultrasound output apparatus 15 which outputs an ultrasound drive signal for causing an ultrasound transducer included in the handpiece 14 to ultrasound-vibrate.

The high-frequency output apparatus 12 and the ultrasound output apparatus 15 are connected via a communication cable 16 so that mutual data communication is possible therebetween.

The handpiece 11 is a treatment instrument having a grasping section 11a, a sheath section 11b extending from the grasping section 11a to a distal end side, and a treatment section (not shown) provided at a distal end portion of the sheath section 11b. A cable 11c extends from a rear end side of the grasping section 11a, and a handpiece connector 11d at a rear end of the cable 11c is detachable from an output connector of the high-frequency output apparatus 12.

Furthermore, a foot switch 17 for specifying high-frequency output is connected to the high-frequency output apparatus 12 via a cable 17a. By pressing down and operating the foot switch 17, a surgeon can perform treatment by a high-frequency current with the treatment section of the handpiece 11.

The handpiece 14 is a treatment instrument having a grasping section 14a provided with a switch (not shown) for specifying ultrasound output, a sheath section 14b extending from the grasping section 14a to a distal end side, and a treatment section (not shown) provided at a distal end portion of the sheath section 14b. A cable 14c extends from a rear end side of the grasping section 14a, and a handpiece connector 14d at a rear end of the cable 14c is detachable from an output connector of the ultrasound output apparatus 15. By pressing down and operating a switch (not shown) provided for the handpiece 14, the surgeon can perform treatment by ultrasound vibration with the treatment section of the handpiece 14.

Note that the ultrasound output apparatus 15 can simultaneously output a high-frequency signal and an ultrasound drive signal when receiving supply of a high-frequency output which is a high-frequency current signal from the high-frequency output apparatus 12. Therefore, two high-frequency cables for communicating the high-frequency signal are inserted through the cable 14c.

Furthermore, the high-frequency output apparatus 12 and the ultrasound output apparatus 15 have speakers 18 and 19, respectively. The high-frequency output apparatus 12 and the ultrasound output apparatus 15 output predetermined sounds from the speakers 18 and 19 at the time when high-frequency output and ultrasound output are being performed, respectively, and the like.

The high-frequency output apparatus 12 and the ultrasound output apparatus 15 are provided with touch panels 20 and 21 having a liquid crystal display device (LCD), respectively, so that display of various pieces of information, instructions and settings are possible.
(Configuration of High-Frequency Output Apparatus)

Figure 2:
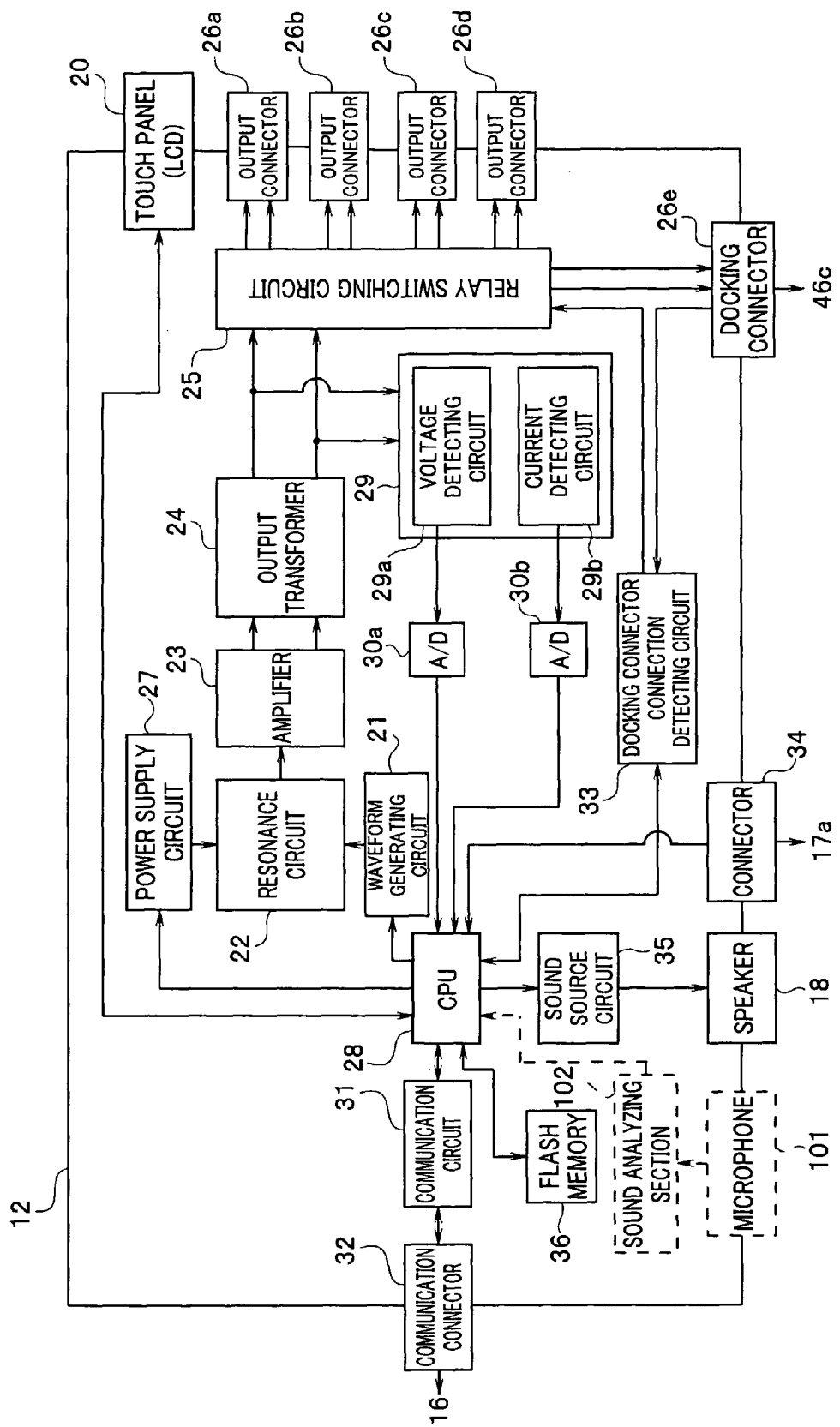
FIG. 2 is a block diagram showing a configuration of a high-frequency output apparatus 12 according to the embodiment of the present invention.

FIG. 2 is a block diagram showing a configuration of the high-frequency output apparatus 12. The high-frequency output apparatus 12, which is a treatment apparatus for performing treatment for a subject, includes a waveform generating circuit 21 for generating a sine wave and a burst wave. A signal of the sine wave or the burst wave outputted from the waveform generating circuit 21 is inputted to an amplifier 23 via a resonance circuit 22.

The signal amplified by the amplifier 23 is applied to a primary winding side of an output transformer 24, and a high-frequency signal, which is a high-frequency output for cauterization, occurs on a secondary winding side.

The secondary winding of the output transformer 24 is connected, for example, to four output connectors 26a, 26b, 26c and 26d and a docking connector 26e via a relay switching circuit 25 for switching outputted high-frequency signals. The docking connector 26e is a female connector and is connected to a male-type docking connector 46c of the ultrasound output apparatus 15 to be described later. The docking connector 26e is provided on a bottom board of a case of the high-frequency output apparatus 12.

Power supply voltage is supplied from a voltage-variable power supply circuit 27 to the resonance circuit 22, and the waveform generating circuit 21 and the power supply circuit 27 are controlled by a central processing unit (hereinafter referred to as a CPU) 28 which is a control section. The CPU 28 controls the waveform generating circuit 21 and the power supply circuit 27 according to setting of an output mode, an output setting value and the like.

An output signal of the secondary winding of the output transformer 24 is inputted to a voltage detecting circuit 29a and a current detecting circuit 29b constituting a detection section 29.

The voltage detecting circuit 29a and the current detecting circuit 29b detect, that is, measure the voltage and current of a high-frequency signal outputted from the secondary winding of the output transformer 24. Detected voltage and current signals are converted to digital voltage and current signals by analog-to-digital converters (hereinafter referred to as A/D converters) 30a and 30b, respectively, and inputted to the CPU 28.

From the inputted voltage and current signals, the CPU 28 detects, that is, calculates high-frequency power, which is a product of the signals. Then, the CPU 28 controls power supply voltage of the power supply circuit 27 so that a value of the detected high-frequency power becomes a setting value set in advance.

The CPU 28 is connected to a communication connector 32 via a communication circuit 31 for performing communication. The communication connector 32 is connected to a communication connector 50 on the ultrasound output apparatus 15 side shown in FIG. 3 via the communication cable 16.

The docking connector 26e connected to the relay switching circuit 25 is detachably connected to the docking connector 46c which is a male connecter on the ultrasound output apparatus 15 side as described above.

For example, two connector pins for connection detection on the docking connector 26e are connected to a docking connector connection detecting circuit 33. The docking connector connection detecting circuit 33 continuously detects connection between the docking connector 26e and the docking connector 46c of the ultrasound output apparatus 15 using the connector pins for connection detection.

In this case, the two connector pins for connection detection are set so as to be connected, for example, to two short-circuit set connector pins on the other docking connector 46c side.

Therefore, by detecting whether the two connector pins for connection detection are in a conduction state or not, connection detection about whether the two docking connectors 26e and 46c are connected to each other or not can be performed.

Then, a result of connection detection by the docking connector connection detecting circuit 33 is communicated to the CPU 28. If the connection detection result by the docking connector connection detecting circuit 35 indicates unconnection, the CPU 28 inhibits simultaneous output of ultrasound output and high-frequency output.

In other words, the CPU 28 permits simultaneous output of ultrasound output and high-frequency output only when connection between the docking connectors 26e and 46c is detected.

If the docking connector connection detecting circuit 33 detects connection between the two docking connectors 26e and 46c, and simultaneous output of ultrasound output and high-frequency output is specified or set, the docking connector connection detecting circuit 33 switches the relay switching circuit 25 so that an output signal of the output transformer 24 is outputted to the docking connector 26e side. Note that not the docking connector connection detecting circuit 33 but the CPU 28 may perform the switching control.

Furthermore, an operation signal from the foot switch 17 is inputted to the CPU 28 via a connector 34 to which the cable 17a is connected.

Furthermore, the speaker 18 of the high-frequency output apparatus 12 is driven by a sound source circuit 35 under the control of the CPU 28. When the foot switch 17 is operated to specify high-frequency output, the CPU 28 controls the sound source circuit 35 so that a sound corresponding to the high-frequency output is outputted at a predetermined output volume level while the specification continues. When an error occurs in the high-frequency output apparatus 12, the CPU 28 controls the sound source circuit 35 so that a sound indicating occurrence of the error is outputted at a predetermined output volume level while the error output continues.

That is, the CPU 28 constitutes an output state detecting section which detects an output state of a predetermined output such as an energy output and an error output. When the predetermined output is detected, the CPU 28 outputs a sound corresponding to the output at a predetermined output volume level. The CPU 28 constitutes a sound output controlling section which, when detecting the predetermined output, controls output of a sound outputted from the speaker 18 according to a state of the detected output. The speaker 18 constitutes a sound outputting section which outputs a sound corresponding to the detected output state.

The touch panel 20 of the high-frequency output apparatus 12 outputs an input signal such as an operation signal and a setting signal to the CPU 28 and displays an image on the screen of the LCD on the basis of an image signal from the CPU 28. A user can set volume of a sound outputted from the speaker 18 using the screen of the touch panel 20.

The high-frequency output apparatus 12 has a flash memory 36 connected to the CPU 28. The flash memory 36 stores a high-frequency output control program, an output volume setting program, various setting values and the like.

Therefore, when the handpiece 11 is connected to the high-frequency output apparatus 12, and the foot switch 17 is pressed down, the CPU 28 controls the waveform generating circuit 21 and the power supply circuit 27 so that a high-frequency output of a value specified or set from the output transformer 24 is outputted from an output connector to which the handpiece 11 is connected. When the high-frequency output is specified, that is, while the foot switch 17 is being pressed down to specify energy output, the CPU 28 continues to output a predetermined sound from the speaker 18.

If an error has occurred in the high-frequency output apparatus 12, the CPU 28 detects the error and drives the sound source circuit 35 to output a predetermined sound corresponding to the error output, from the speaker 18.

Note that the CPU 28 writes information indicating a state of the occurrence of the error into a predetermined storage area of the flash memory 36. For example, when some error occurs in the high-frequency output apparatus 12, the error output is detected by the CPU 28, and the CPU 28 sets a flag of 1 indicating that an error has occurred, in the predetermined storage area. When the cause of the occurrence of the error disappears, the error output is not outputted. Therefore, the CPU 28 rewrites the flag written and set in the predetermined area with 0 indicating that an error does not occur. When the state of the flag indicating existence/nonexistence of an error changes, the CPU 28 performs a process for transmitting flag information to the ultrasound output apparatus 15 via the communication circuit 31.

(Configuration of Ultrasound Output Apparatus)

Figure 3:
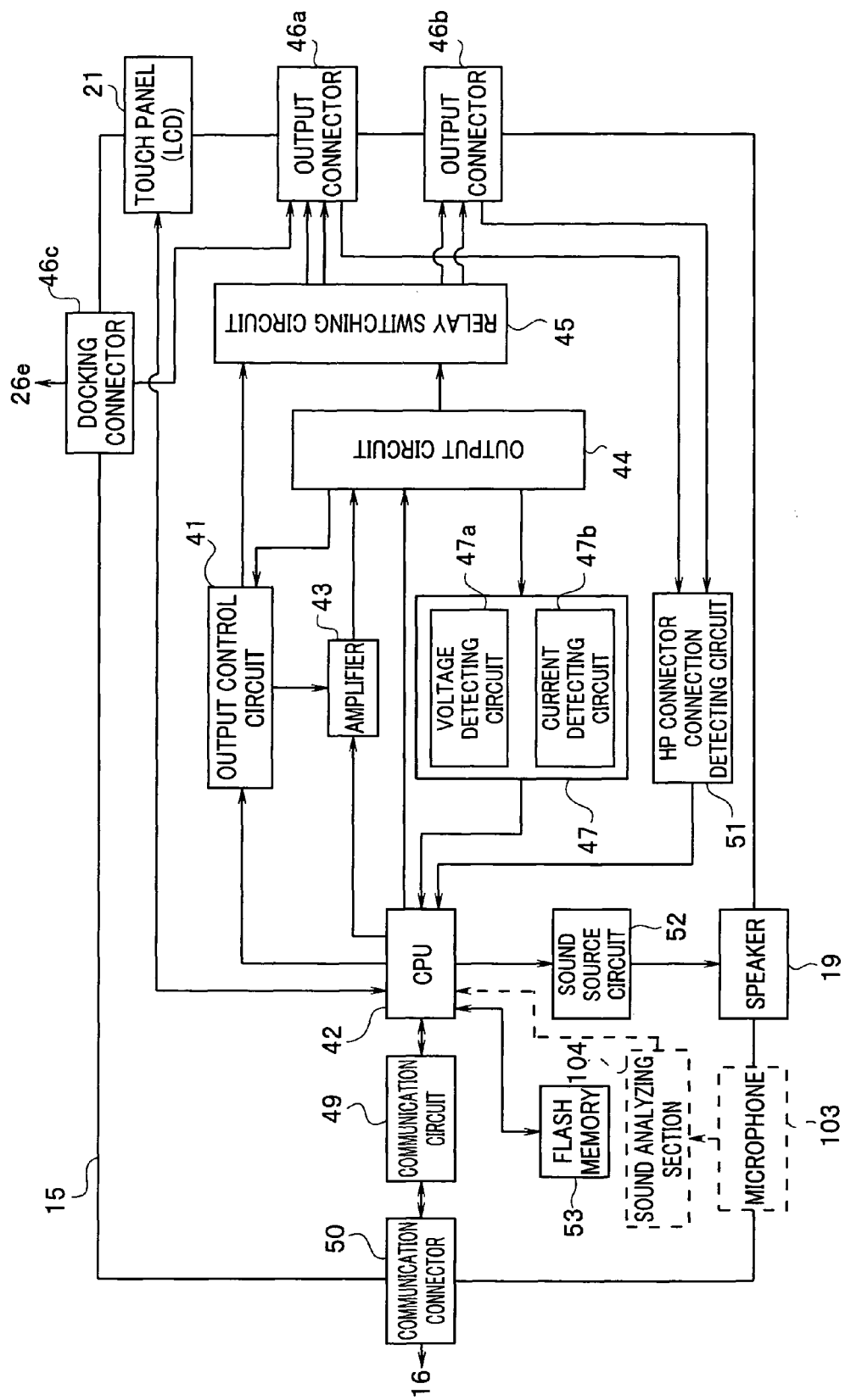
FIG. 3 is a block section showing a configuration of an ultrasound output apparatus 15 according to the embodiment of the present invention.

FIG. 3 is a block section showing a configuration of the high-frequency output apparatus 15. The ultrasound output apparatus 15, which is a treatment apparatus for performing treatment for a subject, has an output control circuit 41 which includes an oscillation circuit. The output control circuit 41 adjusts the frequency and current of an oscillation signal oscillated by the oscillation circuit and outputs the oscillation signal to an amplifier 43 under the control of a CPU 42.

The signal amplified by the amplifier 43 is inputted to an output circuit 44, voltage-amplified by a transformer (not shown) of the output circuit 44 and outputted from a secondary winding of the transformer as an ultrasound drive (output) signal.

The ultrasound drive signal is outputted to two output connectors 46a and 46b via a relay switching circuit 45 which switches and outputs the signal. Note that gain of the amplifier 43 is controlled by the CPU 42.

The output connector 46a, one of the two output connectors, is also connected to the docking connector 46c which is a male connector. The docking connector 46c is provided on a top board of a case of the ultrasound output apparatus 15. A handpiece capable of outputting a monopolar high-frequency current can be connected to the output connector 46a. Note that, though description will be made here on a case where the ultrasound output apparatus 15 and the handpiece 14 output a monopolar high-frequency current, the ultrasound output apparatus 15 and the handpiece 14 may output a bipolar high-frequency current.

Note that the output connector 46b is not connected to the docking connector 46c, but a handpiece exclusive for ultrasound waves which outputs ultrasound waves independently from the high-frequency output apparatus 12 is connected.

An ultrasound drive signal outputted from the output circuit 44 is inputted to a voltage detecting circuit 47a and a current detecting circuit 47b constituting a detection section 47, and voltages and currents are detected, that is, measured, respectively. The detected voltages and currents are inputted to the CPU 42 via A/D converters in the voltage detecting circuit 47a and the current detecting circuit 47b, respectively.

The CPU 42 performs constant current control via the output control circuit 41 on the basis of the voltages and currents detected by the detection section 47 so that set power is outputted from the output circuit 44.

Therefore, control information about an output value at the time of being outputted from the output circuit 44 is temporarily held in a memory in the output control circuit 41, and the CPU 42 performs control so that last control information is corrected via the output control circuit 41 by voltages and currents detected after that.

The CPU 42 is connected to the communication connector 50 via a communication circuit 49 for performing communication. The communication connector 50 is connected to the communication connector 32 on the high-frequency output apparatus 12 side shown in FIG. 2 via the communication cable 16. Thus, the CPU 42 and the CPU 28 can perform transmission and reception with each other via the communication cable 16.

Connector connection detecting pins on the two output connectors 46a and 46b are connected to a handpiece connector connection detecting circuit (hereinafter referred to as an HP connector connection detecting circuit) 51. The HP connector connection detecting circuit 51 detects connection/unconnection of the handpiece connector 14d to the output connectors 46a and 46b and outputs a result of the detection to the CPU 42.

The CPU 42 controls switching of the relay switching circuit 45 via the output control circuit 41 so that an output signal from the output circuit 44 (that is, an ultrasound drive signal) is supplied to an output connector to which the handpiece is connected, on the basis of information about the detection result. Note that the CPU 42 may directly control switching of the relay switching circuit 45.

Furthermore, the ultrasound output apparatus 15 has the speaker 19 driven by a sound source circuit 52. When the switch of the handpiece 14 is operated to specify ultrasound output, the CPU 42 controls the sound source circuit 52 so that a sound corresponding to the ultrasound output is outputted at a predetermined output volume level while the specification continues. When an error occurs in the ultrasound output apparatus 15, the CPU 42 controls the sound source circuit 52 so that a sound indicating occurrence of the error is outputted at a predetermined output volume level while the error output continues.

That is, the CPU 42 constitutes an output state detecting section which detects an output state of a predetermined output such as an energy output and an error output. When the predetermined output is detected, the CPU 42 outputs a sound corresponding to the output at a predetermined output volume level. The CPU 42 constitutes a sound output controlling section which, when detecting the predetermined output, controls output of a sound outputted from the speaker 19 according to the detected output state. The speaker 19 constitutes a sound outputting section which outputs a sound corresponding to the detected output state.

The touch panel 21 of the ultrasound output apparatus 15 outputs an input signal such as an operation signal and a setting signal to the CPU 42 and displays an image on the screen of the LCD on the basis of an image signal from the CPU 42. The user can set volume of a sound outputted from the speaker 19 using the screen of the touch panel 21.

The ultrasound output apparatus 15 has a flash memory 53 connected to the CPU 42. The flash memory 53 stores an ultrasound output control program, an output volume setting program, various setting values and the like.

Therefore, when the handpiece 14 is connected to the ultrasound output apparatus 15, and a switch (not shown) for specifying ultrasound output is pressed down, an ultrasound output instruction signal is inputted to the CPU 42 via an output connector to which the handpiece 14 is connected and the HP connector connection detecting circuit 51. The CPU 42 controls the output control circuit 41 so that an ultrasound output of a value specified or set from the output circuit 44 is outputted from an output connector to which the handpiece 14 is connected.

When a switch (not shown) for specifying ultrasound output is pressed down while simultaneous output of high-frequency output and ultrasound output is specified or set, the CPU 42 controls the output control circuit 41 for ultrasound output as well as specifying high-frequency output to the CPU 28 of the high-frequency output apparatus 12 via the communication circuit 49 and the communication cable 16. When receiving a high-frequency output instruction from the ultrasound output apparatus 15 via the communication cable 16 and the communication circuit 31, the high-frequency output apparatus 12 controls the power supply circuit 27, the waveform generating circuit 21 and the docking connector connection detecting circuit 33 to supply high-frequency output of the relay switching circuit 25 to the ultrasound output apparatus 15 via the docking connectors 26e and 46c. As a result, ultrasound output and high-frequency output are simultaneously outputted from the output connector 46a.

When ultrasound output is being specified, that is, while the switch of the handpiece 14 is being pressed down to specify energy output, the CPU 42 continues to output a predetermined sound from the speaker 19.

If an error has occurred in the ultrasound output apparatus 15, the CPU 42 detects the error and drives the sound source circuit 52 to output a predetermined error sound from the speaker 19. At the same time, the CPU 42 writes information indicating a state of the occurrence of the error into a predetermined storage area of the flash memory 53. For example, when some error occurs in the ultrasound output apparatus 15, the error output is detected by the CPU 42, and the CPU 42 sets a flag of 1 indicating that an error has occurred, in the predetermined storage area. When the cause of the occurrence of the error disappears, the error output is not outputted. Therefore, the CPU 42 rewrites the flag written and set in the predetermined area with 0 indicating that an error does not occur. When the state of the flag indicating existence/nonexistence of an error changes, the CPU 42 performs a process for transmitting flag information to the high-frequency output apparatus 12 via the communication circuit 49.

Note that, as for an output volume level, it is set in advance which of the high-frequency output apparatus 12 and the ultrasound output apparatus 15 is a master apparatus, and information indicating being the master apparatus is recorded in the flash memory of the apparatus set or specified as the master apparatus. Setting of the master apparatus is performed, for example, by displaying a setting screen therefor on the touch panel and causing the user to make a selection. Here, description will be made on the assumption that the ultrasound output apparatus 15 is set as the master apparatus.

(Setting of Output Volume Level)

Next, volume setting in the high-frequency output apparatus 12 and the ultrasound output apparatus 15 will be described. Volume levels of sounds outputted from the speakers 18 and 19, that is, output volume levels can be set in the high-frequency output apparatus 12 and the ultrasound output apparatus 15, respectively.

Figure 4:
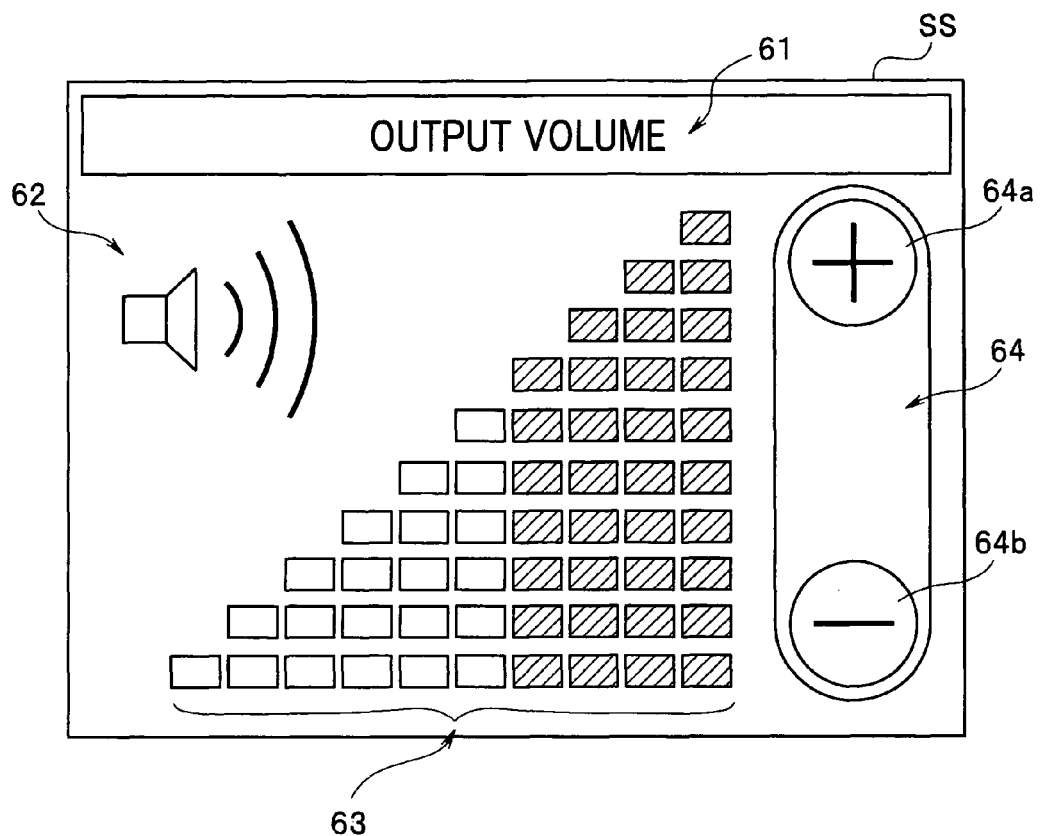
FIG. 4 is a diagram showing an example of an output volume setting screen displayed on touch panels 20 and 21 according to the embodiment of the present invention.

FIG. 4 is a diagram showing an example of an output volume setting screen displayed on the touch panels 20 and 21. For example, when a user such as a surgeon performs a predetermined operation or inputting a command from a predetermined menu screen displayed on the screen of the touch panel 20 of the high-frequency output apparatus 12, an output volume setting/changing screen SS in FIG. 4 is displayed on the screen of the touch panel 20. The output volume setting/changing screen SS may be displayed on the whole screen of the touch panel 20, may be displayed as a part of the screen, or may be displayed as a popup window on the screen.

The output volume setting/changing screen SS includes displaying of characters 61 indicating that the screen is a screen for setting/changing an output volume and a speaker icon 62 as well as a level displaying section 63 indicating which level among multiple levels an output volume level corresponds to and an operation button displaying section 64 for changing the level. The operation button displaying section 64 includes a + (plus) button 64a and a − (minus) button 64b.

The level displaying section 63 indicates, by a bar level, which level among multiple stages (here, 10 stages) an output volume level set currently corresponds to. In FIG. 4, it is shown by display of six bars on the left side in which one to six white blocks are vertically arranged and four bars on the right side in which seven to ten oblique-lined blocks are vertically arranged, that the output volume level is set to level 6.

For example, when the user touches the + (plus) button 64a of the operation button displaying section 64 once, the output volume level increases by one level. When the output volume level increases by one level in the display state of FIG. 4, the level displaying section 63 shows display of seven bars on the left side in which one to seven white blocks are vertically arranged and three bars on the right side in which eight to ten oblique-lined blocks are vertically arranged. The display contents of the level displaying section 63 are changed to a state of displaying that the output volume level is set to level 7.

Similarly, when the user touches the − (minus) button 64b of the operation button displaying section 64 once, the output volume level decreases by one level. When the output volume level decreases by one level in the display state of FIG. 4, the level displaying section 63 shows display of five bars on the left side in which one to five white blocks are vertically arranged and five bars on the right side in which six to ten oblique-lined blocks are vertically arranged. The display contents of the level displaying section 63 are changed to a state of displaying that the output volume level is set to level 5.

When the setting of the output volume level is changed, the CPU 28 writes and stores data of the changed output volume level into the flash memory 36 as well as transmitting the data of the changed output volume level to the ultrasound output apparatus 15 via the communication circuit 31. Then, when setting of an output volume level of a sound outputted from the speaker 18 is performed in the high-frequency output apparatus 12, the same output volume level of a sound outputted from the speaker 19 is changed in the ultrasound output apparatus 15 also to the same level as the output volume level for which setting has been changed in the high-frequency output apparatus 12.

On the touch panel 21 of the ultrasound output apparatus 15 as well, the user can change setting of an output volume level of a sound outputted from the speaker 19 similarly. When the output volume level of a sound is changed in the ultrasound output apparatus 15, the CPU 42 writes and stores data of the changed output volume level into the flash memory 53 as well as transmitting the data of the changed output volume level to the high-frequency output apparatus 12 via the communication circuit 49. Then, when setting of an output volume level for a sound outputted from the speaker 19 is performed in the ultrasound output apparatus 15, the same output volume level of a sound outputted from the speaker 18 is also changed to the same level as the output volume level for which setting has been changed in the ultrasound output apparatus 15, in the high-frequency output apparatus 12 also.

Thus, when setting of an output volume level of a sound outputted from a speaker is changed in any one of the high-frequency output apparatus 12 and the ultrasound output apparatus 15, the same output volume level of a sound outputted from a speaker is changed in the other apparatus also to the same output volume level as the output volume level changed in the one apparatus.

Here, when the high-frequency output apparatus 12 and the ultrasound output apparatus 15 are set to the same output volume level, output volumes of sounds outputted from the two speakers 18 and 19 are the same. However, there may be a case where a value of an output volume level set for the high-frequency output apparatus 12 and the ultrasound output apparatus 15 does not correspond to an output volume of sounds actually outputted. For example, there may be a case where an output volume of a sound actually outputted when the high-frequency output apparatus 12 is set to a level five, is equal to an output volume of a sound actually outputted when the ultrasound output apparatus 15 is set to level 7.

In such a case, each of the high-frequency output apparatus 12 and the ultrasound output apparatus 15 has information about correspondence between its own output volume level and an output volume level of the counterpart, and, when receiving information about an output volume level for which setting has been changed, from the counterpart, each of the apparatuses 12 and 15 may change its own output volume level on the basis of the correspondence information so that output volumes of sounds actually outputted from itself and the counterparts are equal to each other.

(Output Volume Level Linkage Process)

Next, an output volume level linkage process will be described. Here again, description will be made on the case where the ultrasound output apparatus 15 is set as the master apparatus for an output volume level in advance.

(At Startup)

Figure 5:
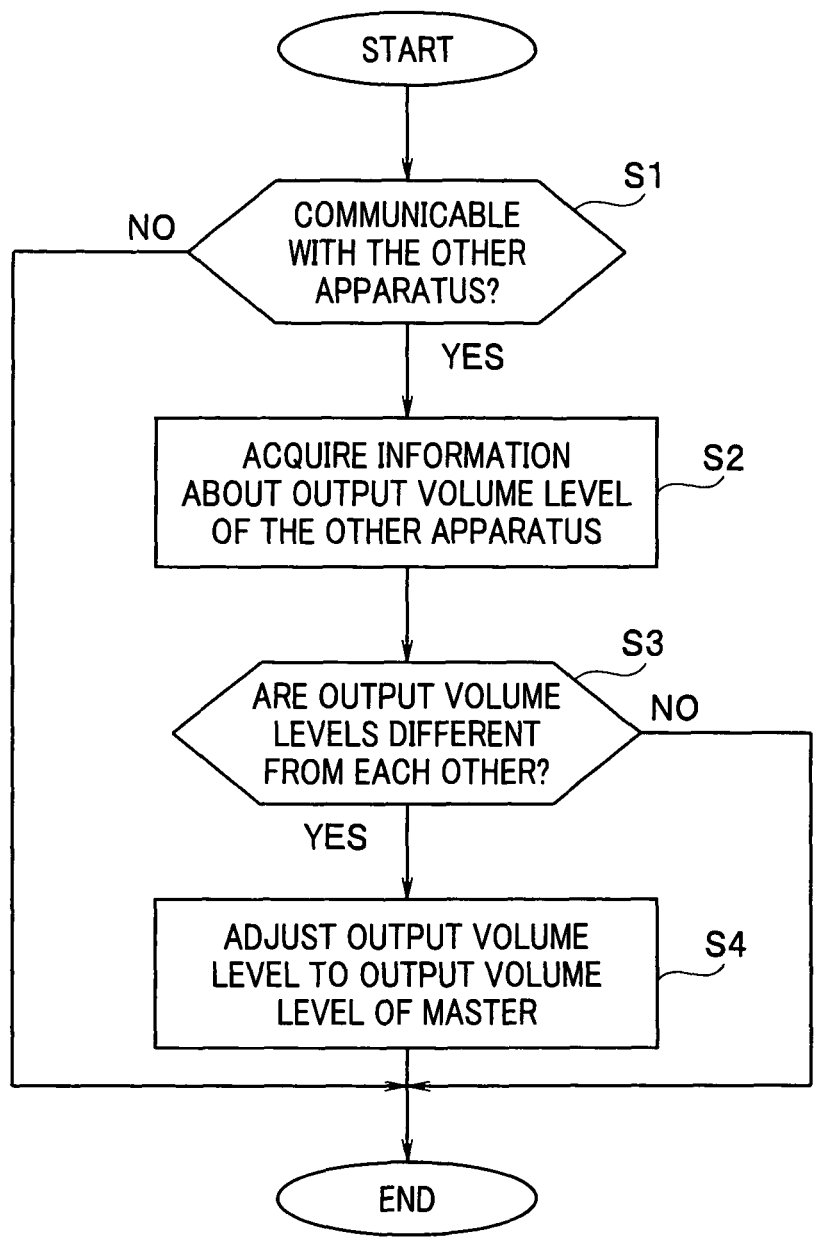
FIG. 5 is a flowchart showing an example of a flow of a process for setting an output volume level at the time of startup of the high-frequency output apparatus 12 and the ultrasound output apparatus 15, according to the embodiment of the present invention.

FIG. 5 is a flowchart showing an example of a flow of a process for setting an output volume level at the time of startup of the high-frequency output apparatus 12 and the ultrasound output apparatus 15. When power switches are turned on, and the high-frequency output apparatus 12 and the ultrasound output apparatus 15 are started up, respectively, the CPUs 28 and 42 read out a startup time volume setting program from the flash memories 36 and 53, respectively, and execute the program.

After executing a predetermined initial process, each of the CPUs (28 and 42) judges whether or not the apparatus is in a state of capable of communicating with the other apparatus (S1). If communication with the other apparatus via the communication cable 16 is established through the communication circuit 31 (49), it is judged that communication is possible. If communication with the other apparatus is impossible, each CPU does not execute a process at and after S2 on the assumption that the apparatus is not connected to the other apparatus (S1: NO).

If communication with the other apparatus is possible (S1: YES), each CPU (28 or 42) transmits a command inquiring about an output volume level to the other apparatus and acquires information about the output volume level of the other apparatus. In this case, both of the two CPUs 28 and 42 acquire the output volume level information from the counterpart, and the communication circuit of each of the high-frequency output apparatus 12 and the ultrasound output apparatus 15 constitutes an output volume information transmitting section which transmits sound output volume information and constitutes an output volume information receiving section which receives the transmitted output volume information and communicates the output volume information to the CPU which is a sound output controlling section.

When acquiring the output volume level information about the other apparatus, each CPU compares the information with its own output volume level and judges whether or not its own output volume level is different from the output volume level of the other apparatus (S3).

If its own output volume level is different from the output volume level of the other apparatus (S3: YES), each CPU adjusts its own output volume level to the output volume level of the master (S4). That is, the CPU of an apparatus which is not the master controls an output volume of a sound outputted from the speaker on the basis of the received output volume information, and controls the output volume of its own speaker on the basis of the received output volume information so that the output volume of the speaker of the apparatus which is the master and the output volume of its own speaker correspond to each other.

Here, since the ultrasound output apparatus 15 is set in advance as a master apparatus for an output volume level, information indicating that the ultrasound output apparatus 15 is a master apparatus is recorded in the flash memory 53. By reading out the information indicating that the ultrasound output apparatus 15 is a master apparatus from the flash memory 53, the ultrasound output apparatus 15 can judge that the ultrasound output apparatus 15 itself is a master apparatus. Therefore, the ultrasound output apparatus 15 does not perform the process for adjusting the output volume level to the output volume level of the high-frequency output apparatus 12 which is not a master apparatus. That is, the CPU 42 of the ultrasound output apparatus 15 which is the master apparatus does not execute the processing of S4.

On the other hand, since the information indicating being a master apparatus is not recorded in the flash memory 36, the CPU 28 of the high-frequency output apparatus 12 adjusts its own output volume level to the output volume level information about the ultrasound output apparatus 15 and writes and records the output volume level information into the flash memory 36. For example, when the output volume level is set to 7 in the high-frequency output apparatus 12 but the output volume level of the ultrasound output apparatus 15 which is a master apparatus is 5, the CPU 28 changes its own output volume level to 5.

If its own output volume level is not different from the output volume level of the other apparatus (S3: NO), the process ends.

As described above, the output volume levels of the high-frequency output apparatus 12 and the ultrasound output apparatus 15 are set to the same level at startup of the high-frequency output apparatus 12 and the ultrasound output apparatus 15.

(During Use)

Figure 6:
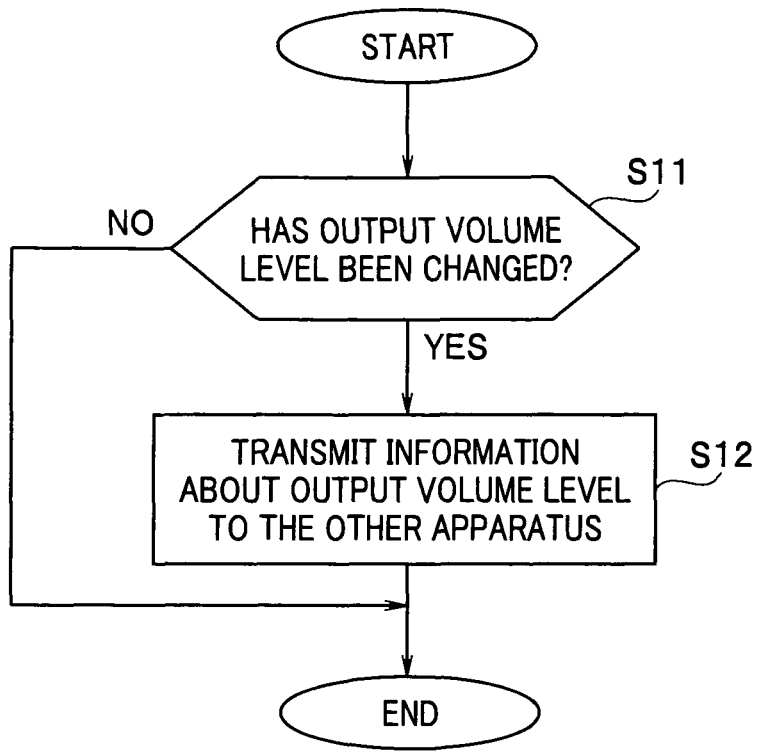
FIG. 6 is a flowchart showing an example of a flow of a notification process for, when the output volume level is changed in one of the high-frequency output apparatus 12 and the ultrasound output apparatus 15 during use of the high-frequency output apparatus 12 and the ultrasound output apparatus 15, notifying the other that the change has been made, according to the embodiment of the present invention.

FIG. 6 is a flowchart showing an example of a flow of a notification process for, when the output volume level is changed in one of the high-frequency output apparatus 12 and the ultrasound output apparatus 15 during use of the high-frequency output apparatus 12 and the ultrasound output apparatus 15, notifying the other that the change has been made. Each of the high-frequency output apparatus 12 and the ultrasound output apparatus 15 judges whether or not the output volume level has been changed in its own apparatus (S11). As described above, an output volume level change is made on the output volume setting changing screen SS shown in FIG. 4.

Since each CPU has output volume level information stored in its flash memory, the CPU monitors the information and can judge that the output volume level is changed when the information is rewritten.

When the output volume level is changed (S11: YES), each CPU transmits information about the changed output volume level to the other apparatus via the communication circuit (S12) to notify the other apparatus thereof. For example, when the output volume level is changed in the high-frequency output apparatus 12, the CPU 28 transmits information about the changed output volume level to the ultrasound output apparatus 15. Thus, in this case, the communication circuit 31 of the high-frequency output apparatus 12 constitutes an output volume information transmitting section which transmits output volume information about a sound to the ultrasound output apparatus 15. If the output volume level is not changed (S11: NO), each CPU does not perform any processing.

Figure 7:
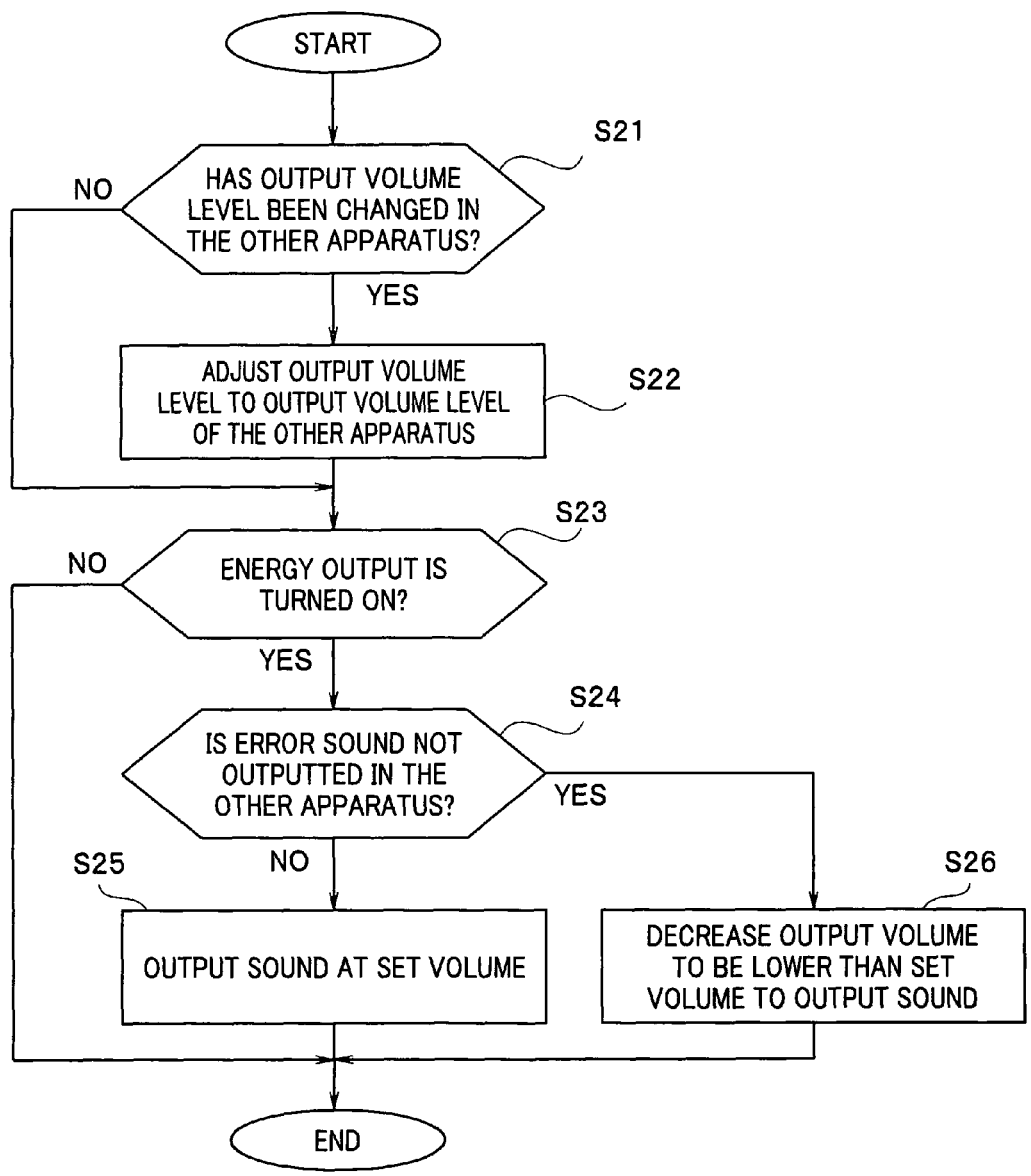
FIG. 7 is a flowchart showing an example of a flow of an output volume level changing process at the time when the output volume level is changed in the other apparatus during use of the high-frequency output apparatus 12 and the ultrasound output apparatus 15 and a sound output process at the time when energy output is specified, according to the embodiment of the present invention.

FIG. 7 is a flowchart showing an example of a flow of an output volume level changing process at the time when the output volume level is changed in the other apparatus during use of the high-frequency output apparatus 12 and the ultrasound output apparatus 15 and a sound output process at the time when energy output is specified.

Each of the high-frequency output apparatus 12 and the ultrasound output apparatus 15 judges whether or not the output volume level has been changed in the other apparatus (S21). Whether the output volume level has been changed or not in the other apparatus can be judged on the basis of the information transmitted at S12 in FIG. 6. Thus, the communication circuit which receives the transmitted information constitutes an output volume information receiving section which receives transmitted output volume information and communicates the output volume information to the CPU which is a sound output controlling section.

If the output volume level has been changed in the other apparatus (S21: YES), each CPU performs a process for adjusting its own output volume level to the output volume level changed in the other apparatus (S22). Thus, each CPU, which is a sound output controlling section, controls output volume of a sound outputted from the speaker so as to adjust its own output volume level to the output volume level changed in the other apparatus on the basis of received output volume information.

After the processing of S22, the process proceeds to S23. If the output volume level has not been changed in the other apparatus (S21: NO), each CPU executes processing of S23.

At S23, each CPU judges whether energy output has been turned on or not. For example, the judgment is performed on the basis of whether the foot switch 17 has been pressed down or not in the high-frequency output apparatus 12. In the ultrasound output apparatus 15, the judgment is performed on the basis of whether the switch (not shown) for specifying ultrasound output, which is provided for the grasping section 14a of the handpiece 14, has been pressed down or not. If energy output is not turned on (S23: NO), each CPU does not perform any processing.

If energy output is turned on (S23: YES), each CPU judges whether or not an error sound is not outputted in the other apparatus (S24). Whether an error sound is outputted or not is judged on the basis of flag information indicating occurrence of an error transmitted from the other apparatus.

If an error sound is not outputted in the other apparatus (S24: NO), each CPU outputs a predetermined sound at a set output volume level (S25). In the case of the high-frequency output apparatus 12, a sound indicating that energy output is performed is outputted from the speaker 18 at the set output volume level. In the case of the ultrasound output apparatus 15, a sound indicating that energy output is being performed is outputted from the speaker 19 at the set output volume level. The output volume level of the high-frequency output apparatus 12 is the same as the output volume level of the ultrasound output apparatus 15.

If an error sound is outputted in the other apparatus (S24: YES), each CPU decreases the output volume level lower than the set output volume level to output a sound (S26). In the case of the high-frequency output apparatus 12, since the ultrasound output apparatus 15 is outputting an error sound, a sound indicating that energy output is being performed is outputted from the speaker 18 at an output volume level lower than the set output volume level. In the case of the ultrasound output apparatus 15, since the high-frequency output apparatus 12 is outputting an error sound, a sound indicating that energy output is being performed is outputted from the speaker 19 at an output volume level lower than the set output volume level. Thereby, it is possible to certainly cause the user such as a surgeon to let the surgeon know the error sound.

As described above, when a predetermined sound such as an error sound is outputted from the speaker of the other medical apparatus, each CPU, which is a sound output controlling section, controls output volume of a sound outputted from the speaker of its own medical apparatus so as to decrease the output volume of the sound outputted from the speaker of its own apparatus to be lower than output volume of a predetermined sound outputted from the speaker of the other medical apparatus.

Figure 8:
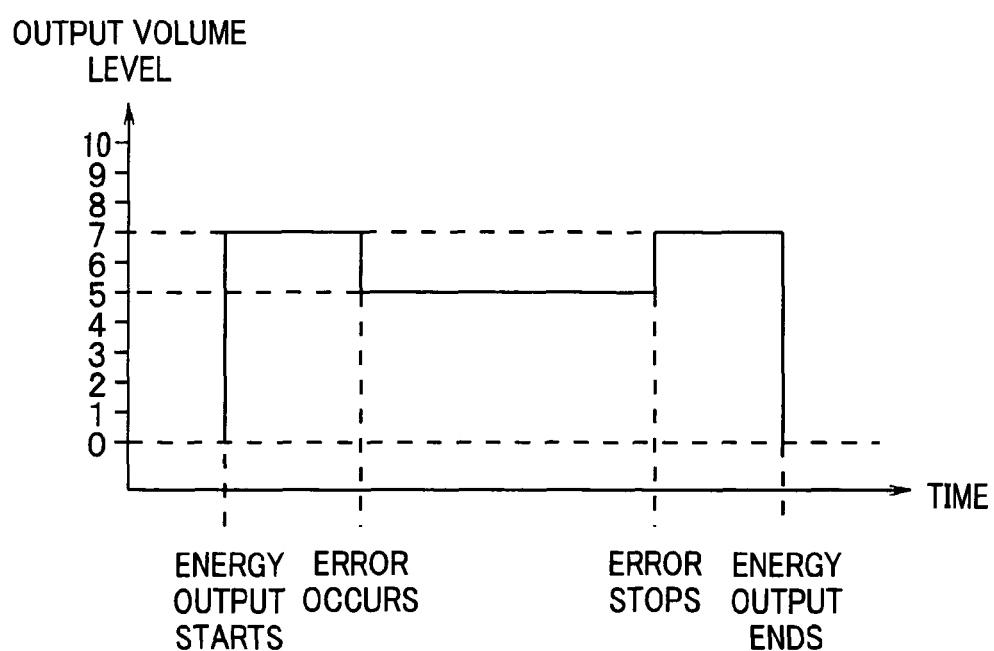
FIG. 8 is a diagram for illustrating change in sound output when energy output is specified, according to the embodiment of the present invention.

FIG. 8 is a diagram for illustrating change in sound output when energy output is specified. For example, when energy output is specified in the high-frequency output apparatus 12, a sound indicating that energy output is being performed is outputted at a set output volume level. In FIG. 8, it is shown that, when energy output is specified, a predetermined sound is outputted at the output volume level 7.

When an error occurs in the ultrasound output apparatus 15 while energy is being outputted, the ultrasound output apparatus 15 outputs an error sound. At the same time, since detecting that the error has occurred in the ultrasound output apparatus 15, the CPU 28 of the high-frequency output apparatus 12 outputs a sound indicating that energy is being outputted at an output volume level by decreasing to be lower than a set output volume level by a predetermined level. In FIG. 8, the sound indicating that energy is being outputted is outputted at an output volume level of level 7. However, when detecting occurrence of an error in the other apparatus, the output volume level is decreased by two levels, and the sound indicating that energy is being outputted is outputted at an output volume level of level 5. After that, since the error stops, that is, the error state disappears, the high-frequency output apparatus 12 returns the sound indicating that energy output is being performed to the output volume level of level 7 to output the sound.

Note that the high-frequency output apparatus 12 and the ultrasound output apparatus 15 are adapted to be able to release the interlock between output volume levels.

Figure 9:
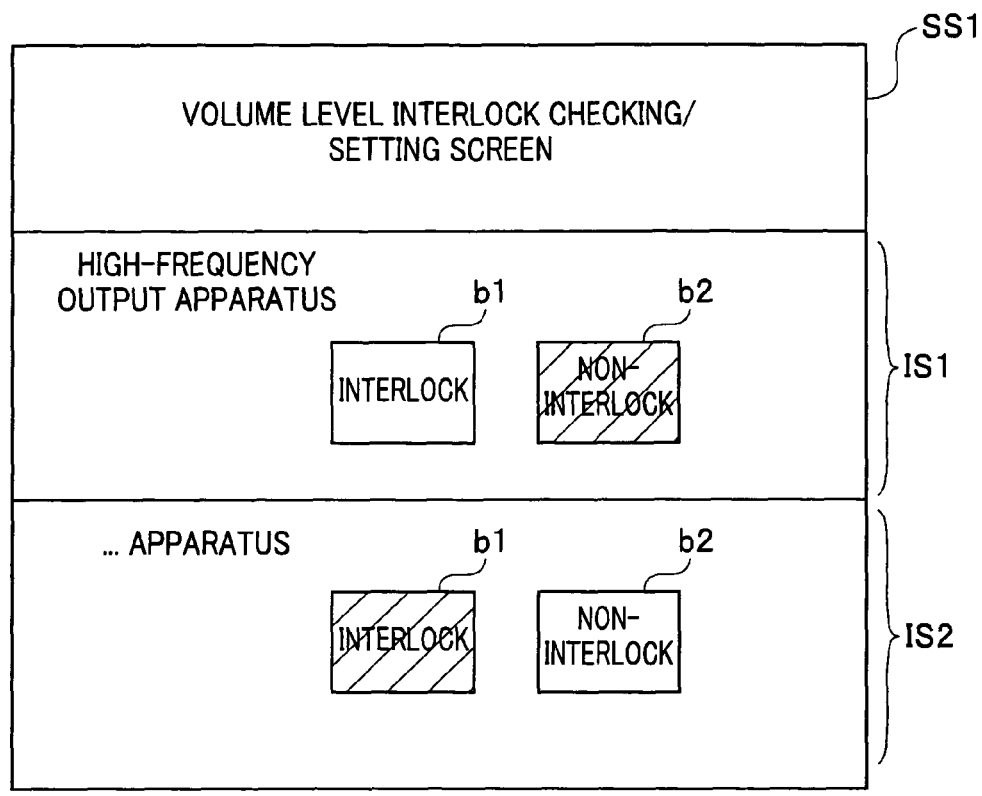
FIG. 9 is a diagram showing an example of a screen for confirming and setting an output volume level interlocking state, according to the embodiment of the present invention.

FIG. 9 is a diagram showing an example of a screen for confirming and setting an output volume level interlocking state. When the user performs a predetermined operation, a volume level checking/setting screen as shown in FIG. 9 is displayed on the screen of the touch panel.

FIG. 9 shows an example of a volume level checking/setting screen SS1 displayed on the touch panel 21 of the ultrasound output apparatus 15. A state of linkage with the high-frequency output apparatus 12 connected to the ultrasound output apparatus 15 via the communication cable 16 is shown in an interlocking state displaying section IS1. An interlock button b1 and a non-interlock button b2 are displayed in the interlocking state displaying section IS1. By the interlock button b1 being displayed bright and the non-interlock button b2 being displayed dark (in FIG. 9, indicated by oblique lines), it is shown that the output volume levels of both of the ultrasound output apparatus 15 and the high-frequency output apparatus 12 are in a linkage state, on the interlocking state displaying section IS1.

By touching the non-interlock button b2 in this state, the user can change the output volume levels of both of the ultrasound output apparatus 15 and the high-frequency output apparatus 12 to a non-interlock state. That is, the user can use the volume level checking/setting screen SS1 to confirm and change setting of the interlock state of the output volume levels of both of the ultrasound output apparatus 15 and the high-frequency output apparatus 12.

Though the high-frequency output apparatus 12 and the ultrasound output apparatus 15 are communicably connected via the communication cable 16 in FIG. 1, each apparatus can communicate with other apparatuses. When interlock/non-interlock between output volume levels can be set, linkage states about the other apparatuses are also displayed in the volume level checking/setting screen SS1 so that linkage/non-linkage setting can be changed. In FIG. 9, it is shown in a linkage state displaying section IS2 that the output volume levels of the ultrasound output apparatus 15 and another apparatus are in a non-interlock state.

Furthermore, note that there may be a case where each of the high-frequency output apparatus 12 and the ultrasound output apparatus 15 has multiple operation modes. In such a case, interlock/non-interlock between output volume levels may be set for each operation mode.

As described above, according to the present embodiment, it is possible to provide a medical system in which interlock or linkage of output volume levels among multiple medical apparatuses is possible. More specifically, it is possible to adjust an output volume level to the same level as the other medical apparatuses, and, furthermore, it becomes possible to, when an error occurs in another medical apparatus, lower the output volume level of a sound indicating that energy output is being performed so that an error sound therefor can be certainly heard, and, thereby, the output volume levels among the multiple medical apparatuses are linked.

Next, a modification of the present embodiment will be described.

(Modification)

In the medical system of the embodiment described above, multiple medical apparatuses are communicably connected, and interlock or linkage between output volume levels is performed with the other medical apparatuses by communication thereof. Furthermore, a medical system of the present modification enables linkage with an output sound of an incommunicable piece of medical equipment.

A high-frequency output apparatus 12 of the present modification has a microphone 101 and a sound analyzing section 102 as shown by broken lines in FIG. 2. The microphone 101 is provided on a case of the high-frequency output apparatus 12 to receive surrounding sounds and output voice signals. The sound analyzing section 102 inputs the voice signal from the microphone 101, analyzes a frequency, generates feature values of the voice signal as a result of the analysis and outputs the feature values to a CPU 28.

Similarly, an ultrasound output apparatus 15 also has a microphone 103 and a sound analyzing section 104. The microphone 103 is provided on a case of the ultrasound output apparatus 15 to receive surrounding sounds and output voice signals. The sound analyzing section 104 inputs the voice signal from the microphone 103, analyzes a frequency, generates feature values of the voice signal as a result of the analysis and outputs the feature values to a CPU 42.

Then, each CPU (28 or 42) can obtain the inputted feature values (including volume) of the voice signal and store the feature values into a corresponding flash memory (36 or 53).

As an apparatus used together with the high-frequency output apparatus 12 and the ultrasound output apparatus 15 and placed in an operating room, there is, for example, an electrocardiograph. The electrocardiograph outputs an error sound when an error occurs. However, there may be a case where communication with the high-frequency output apparatus 12 and the ultrasound output apparatus 15 is impossible. Therefore, it is not possible to inform the high-frequency output apparatus 12 and the ultrasound output apparatus 15 of the error occurrence in the electrocardiograph through communication. When an error occurs in the electrocardiograph during treatment by a high-frequency current or ultrasound vibration, a surgeon is required to quickly cope therewith. Therefore, it is necessary to prevent it from happening that the surgeon cannot hear an error sound of the electrocardiograph due to interruption by a sound indicating that energy output is being performed.

Therefore, in the present modification, the high-frequency output apparatus 12 and the ultrasound output apparatus 15 are provided with the microphones 101 and 103, respectively, and the sound analyzing sections 102 and 104, respectively, and the error sound of the electrocardiograph is stored. The high-frequency output apparatus 12 and the ultrasound output apparatus 15 are configured so as to be capable of detecting occurrence of the error sound of the electrocardiograph.

Figure 10:
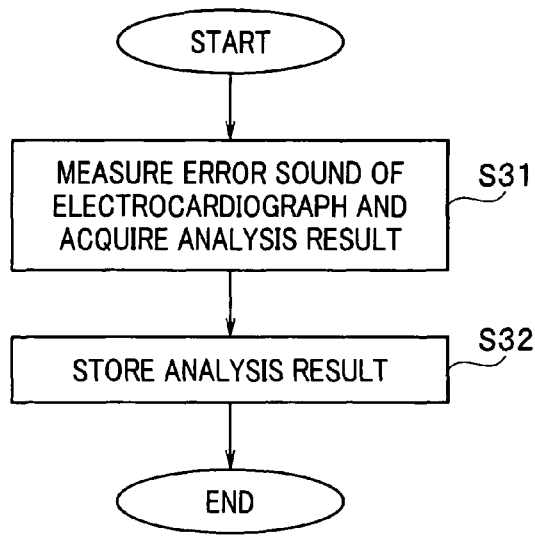
FIG. 10 is a flowchart showing an example of a learning mode process of a high-frequency output apparatus 12 and an ultrasound output apparatus 15 according to a modification of the embodiment of the present invention, according to the present modification.

Each of the high-frequency output apparatus 12 and the ultrasound output apparatus 15 has a learning mode for storing the error sound of the electrocardiograph. FIG. 10 is a flowchart showing an example of a learning mode process of the high-frequency output apparatus 12 and the ultrasound output apparatus 15 according to the present modification. The learning mode of the high-frequency output apparatus 12 will be described below. Since a process of the learning mode of the ultrasound output apparatus 15 is similar, description thereof will be omitted.

When a user performs a predetermined operation against a touch panel 20, the high-frequency output apparatus 12 enters the learning mode.

The user operates an electrocardiograph (not shown) to set a state in which an error sound occurs, and causes the high-frequency output apparatus 12 to execute the learning mode process. The CPU 28 causes the sound analyzing section 102 to analyze a voice signal outputted from the microphone 101, and acquires information about an analysis result including feature value data and volume data of the sound (S31).

The CPU 28 stores the information about the analysis result into the flash memory 36 (S32). As described above, the high-frequency output apparatus 12 obtains, that is, learns the error sound of the electrocardiograph, which is another medical apparatus that is incommunicable, and stores sound information about the error sound into the flash memory 36 which is a storage device.

Figure 11:
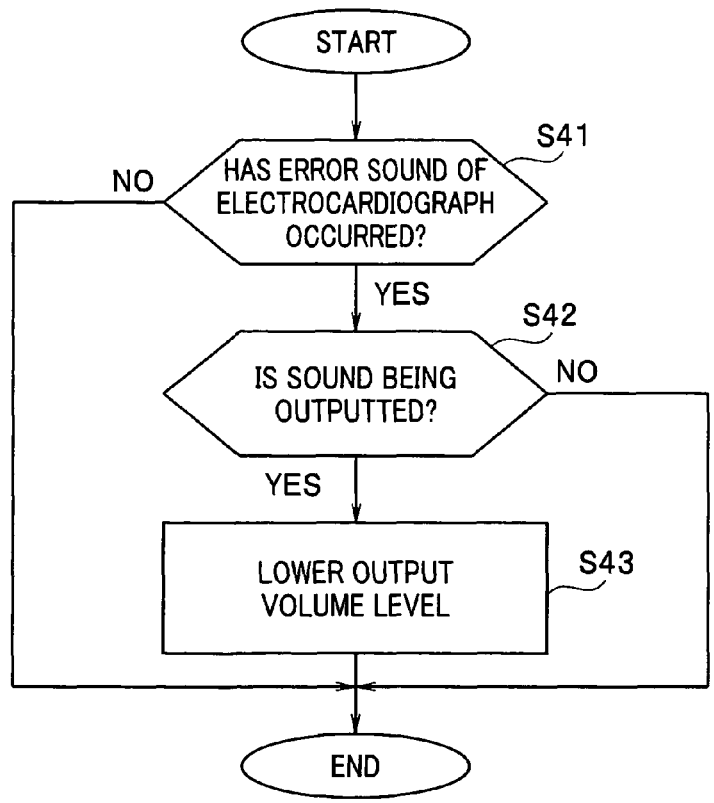
FIG. 11 is a flowchart showing an example of a process at the time of occurrence of an error sound of an electrocardiograph in the high-frequency output apparatus 12 according to the modification of the embodiment of the present invention.

The high-frequency output apparatus 12 adjusts the volume level of its own output on the basis of the error sound of the electrocardiograph stored in the learning mode. FIG. 11 is a flowchart showing an example of a process at the time of occurrence of the error sound of the electrocardiograph in the high-frequency output apparatus 12. The process at the time of occurrence of the error sound of the electrocardiograph in the high-frequency output apparatus 12 will be described below. Since a process at the time of occurrence of the error sound of the electrocardiograph in the ultrasound output apparatus 15 is similar, description thereof will be omitted.

While the high-frequency output apparatus 12 is operating, the CPU 28 judges whether the error sound of the electrocardiograph has occurred or not on the basis of analysis result information from the sound analyzing section 102 (S41). The judgment is performed by comparing information about an analysis result from the sound analyzing section 102, which is inputted in real-time, and information about the error sound of the electrocardiograph stored in the flash memory 36. When the information about an analysis result from the sound analyzing section 102 corresponds to the information about the error sound of the electrocardiograph stored in the flash memory 36, it is judged that the error sound of the electrocardiograph has occurred.

When it is judged that the error sound of the electrocardiograph has not occurred (S41: NO), the process is not executed at all.

When it is judged that the error sound of the electrocardiograph has occurred (S41: YES), the CPU 28 judges whether the sound indicating that energy output is being performed is currently being outputted (S42). When it is judged that the sound indicating that energy output is being performed is currently being outputted (S42: YES), the CPU 28 outputs the sound indicating that energy output is being performed, by lowering the output volume level by a predetermined level (S43). When it is judged that the sound indicating that energy output is being performed is not currently being outputted (S42: NO), the CPU 28 does not do any processing.

As described above, when detecting a predetermined sound outputted from the electrocardiograph as a third medical apparatus, each CPU, which is a sound output controlling section, decreases the output volume of a sound outputted from the speaker of its own medical apparatus to be lower than the output volume of a sound outputted from the electrocardiograph.

Thus, according to the medical system of the present modification, the high-frequency output apparatus 12 and the ultrasound output apparatus 15 can establish linkage between output volume levels by mutual communication as well as establishing linkage with a sound which has occurred in a medical apparatus other than the high-frequency output apparatus 12 and the ultrasound output apparatus 15.

As described above, according to the embodiment and modification described above, it is possible to provide a medical system in which interlock or linkage of output volume levels among multiple medical apparatuses is possible.

The present invention is not limited to the embodiment and modification described above, and various changes, alterations and the like are possible within a range not departing from the spirit of the present invention.

What is claimed is:

1. A medical system comprising a first medical apparatus and a second medical apparatus, the medical system comprising:
- a first output state detecting section provided for the first medical apparatus, the first output state detecting section including a first error detecting section detecting an error of the first medical apparatus and detecting a first output state about a first output;
- a first sound outputting section provided for the first medical apparatus, the first sound outputting section outputting a first sound corresponding to the first output state detected by the first output state detecting section;
- a first output volume information transmitting section provided for the first medical apparatus, the first output volume information transmitting section transmitting first output volume information about the first sound to the second medical apparatus;
- a first error transmitting section provided for the first medical apparatus, the first error transmitting section transmitting a first error signal based on a detection by the first error detecting section;
- a second output state detecting section provided for the second medical apparatus, the second output state detecting section detecting a second output state about a second output;
- a second sound outputting section provided for the second medical apparatus, the second sound outputting section outputting a second sound corresponding to the second output state detected by the second output state detecting section;
- a first output volume information receiving section provided for the second medical apparatus, the first output volume information receiving section receiving the first output volume information and the first error signal;
- a first sound output controlling section setting a reference volume of the second sound to be outputted at the second sound output and controlling an output of the second sound to be outputted from the second sound outputting section, based on the first output volume information, in accordance with the second output state detected by the second output state detecting section; and
- a first output volume adjusting section provided for the first sound output controlling section, the first output volume adjusting section making a setting for lowering the reference volume of the second sound on the basis of the first error signal.

2. The medical system according to claim 1, wherein the first output volume adjusting section adjusts volume of the second sound so that the reference volume of the second sound is at a lower level than a level of the sound indicating the error occurrence in the apparatus from the first sound outputting section.

3. The medical system according to claim 1, wherein the first sound output controlling section sets the reference volume of the second sound outputted at the second sound output so that the reference volume corresponds to volume of the first sound, on the basis of the output volume information.

4. The medical system according to claim 1, comprising:
- a second output volume information transmitting section provided for the second medical apparatus, the second output volume information transmitting section including a second error detecting section detecting an error of the second medical apparatus and transmitting second output volume information about the second sound to the first medical apparatus;
- a second error transmitting section provided for the second medical apparatus, the second error transmitting section transmitting a second error signal based on the detection by the second error detecting section;
- a second output volume information receiving section provided for the first medical apparatus, the second output volume information receiving section receiving the second output volume information and the second error signal;
- a second sound output controlling section setting a reference volume of the first sound to be outputted at the first sound output and controlling an output of the first sound to be outputted from the first sound outputting section, based on the second output volume information, in accordance with the second output state detected by the second output state detecting section; and
- a second output volume adjusting section provided for the first sound output controlling section, the second output volume adjusting section making a setting for lowering the reference volume of the first sound on the basis of the second error signal.

5. The medical system according to claim 4, wherein the second output controlling section sets the reference volume of the second sound outputted at the first sound output so that the reference volume corresponds to volume of the second sound, on the basis of the second output volume information.

6. The medical system according to claim 4, wherein, when detecting a sound outputted from a third medical apparatus, the second sound output controlling section decreases the output volume of the first sound outputted from the first sound outputting section to be lower than output volume of a sound outputted from the third medical apparatus.

7. The medical system according to claim 6, wherein the third medical apparatus is an electrocardiograph.

8. The medical system according to claim 1, wherein the second output volume adjusting section adjusts volume of the first sound so that the reference volume of the first sound is at a lower level than that of the sound indicating the error occurrence in the apparatus from the second sound outputting section.

9. The medical system according to claim 1, wherein
- each of the first medical apparatus and the second medical apparatus is a treatment apparatus for performing treatment for a subject; and
- a sound outputted by the first sound outputting section and the second sound outputting section is a sound indicating that energy output for the treatment is being performed, in each of the first medical apparatus and the second medical apparatus.

10. The medical system according to claim 1, wherein, when detecting a sound outputted from a third medical apparatus, the first output volume adjusting section decreases output volume of the second sound outputted from the second sound outputting section to be lower than output volume of a sound outputted from the third medical apparatus.

11. The medical system according to claim 10, wherein the third medical apparatus is an electrocardiograph.

12. The medical system according to claim 1, wherein, when an error occurrence has stopped in the first sound outputting section, the first output volume adjusting section returns the second sound to the reference volume.

* * * * *